(12) United States Patent
Deo et al.

(10) Patent No.: US 10,222,936 B2
(45) Date of Patent: Mar. 5, 2019

(54) BEVERAGE DISPENSING DEVICE WITH GRAPHICAL REPRESENTATION OF CUSTOMIZED BEVERAGE SELECTION

(71) Applicant: PepsiCo, Inc., Purchase, NY (US)

(72) Inventors: Indrani Deo, Ossining, NY (US); Steven Jersey, Laguna Niguel, CA (US)

(73) Assignee: PepsiCo, Inc., Purchase, NY (US)

( * ) Notice: Subject to any disclaimer, the term of this patent is extended or adjusted under 35 U.S.C. 154(b) by 316 days.

(21) Appl. No.: 14/341,225

(22) Filed: Jul. 25, 2014

(65) Prior Publication Data

US 2014/0337795 A1   Nov. 13, 2014

Related U.S. Application Data

(63) Continuation of application No. 13/947,557, filed on Jul. 22, 2013, now Pat. No. 8,798,799, which is a continuation of application No. 12/703,003, filed on Feb. 9, 2010, now Pat. No. 8,490,829, which is a
(Continued)

(51) Int. Cl.
| | |
|---|---|
| *G06F 3/0482* | (2013.01) |
| *B67D 1/00* | (2006.01) |
| *B67D 1/12* | (2006.01) |
| *G07F 9/00* | (2006.01) |
| *G07F 11/00* | (2006.01) |
| *G07F 13/06* | (2006.01) |

(Continued)

(52) U.S. Cl.
CPC ......... *G06F 3/0482* (2013.01); *B67D 1/0027* (2013.01); *B67D 1/0032* (2013.01); *B67D 1/0034* (2013.01); *B67D 1/0041* (2013.01); *B67D 1/1234* (2013.01); *G07F 9/00* (2013.01); *G07F 11/002* (2013.01); *G07F 13/065* (2013.01); *A61B 5/0002* (2013.01); *B67D 1/0888* (2013.01); *B67D 2210/00089* (2013.01)

(58) Field of Classification Search
CPC .................................................. G06F 3/4082
USPC ........................................................ 715/771
See application file for complete search history.

(56) References Cited

U.S. PATENT DOCUMENTS

| | | |
|---|---|---|
| 5,103,649 A | 4/1992 | Kieffer |
| 5,154,586 A | 10/1992 | Rudick |
| 6,304,797 B1 | 10/2001 | Shusterman |

(Continued)

FOREIGN PATENT DOCUMENTS

| | | |
|---|---|---|
| CA | 2492602 A1 | 7/2006 |
| GB | 2442223 A | 4/2008 |

(Continued)

*Primary Examiner* — Roland J Casillas
(74) *Attorney, Agent, or Firm* — Sterne, Kessler, Goldstein & Fox P.L.L.C.

(57) ABSTRACT

Systems and methods for dispensing compositions, such as beverages, are provided. A beverage dispenser may be configured to receive input corresponding to a selection of a beverage, and in response, a graphical representation of the beverage at a display device. The beverage dispenser may receive additional input corresponding to an adjustment of an amount of an ingredient of the selected beverage, and in response, the graphical representation of the beverage may be updated. The graphical representation of the beverage may include graphics depicting the beverage container, the volume of liquid in the beverage container, and the adjusted ingredient.

19 Claims, 7 Drawing Sheets

Related U.S. Application Data continuation-in-part of application No. 12/625,226, filed on Nov. 24, 2009, now Pat. No. 8,335,592.

(51) Int. Cl.
  *A61B 5/00* (2006.01)
  *B67D 1/08* (2006.01)

(56) References Cited

U.S. PATENT DOCUMENTS

| | | |
|---|---|---|
| 6,591,664 B2 | 7/2003 | Litton |
| 7,156,259 B2 | 1/2007 | Bethuy et al. |
| 7,295,889 B2 | 11/2007 | Lahteenmaki |
| 7,762,181 B2 | 7/2010 | Boland et al. |
| 7,806,294 B2 | 10/2010 | Gatipon et al. |
| 8,335,592 B2 | 12/2012 | Deo et al. |
| 8,490,829 B2 | 7/2013 | Deo et al. |
| 2003/0173370 A1 | 9/2003 | Park |
| 2004/0144423 A1 | 7/2004 | Everett et al. |
| 2005/0035152 A1 | 2/2005 | Bethuy et al. |
| 2005/0048461 A1 | 3/2005 | Lahteenmaki |
| 2005/0119540 A1 | 6/2005 | Potts et al. |
| 2005/0133420 A1 | 6/2005 | Rinker et al. |
| 2005/0145650 A1 | 7/2005 | Henry et al. |
| 2005/0199646 A1 | 9/2005 | Moy |
| 2006/0051296 A1 | 3/2006 | Holahan |
| 2006/0097009 A1 | 5/2006 | Bethuy et al. |
| 2006/0099310 A1 | 5/2006 | Koekkoek |
| 2006/0173260 A1 | 8/2006 | Gaoni et al. |
| 2006/0231109 A1 | 10/2006 | Howell et al. |
| 2007/0073557 A1 | 3/2007 | Abramson |
| 2007/0093553 A1 | 4/2007 | Baxter et al. |
| 2007/0114244 A1 | 5/2007 | Gatipon et al. |
| 2007/0205220 A1 | 9/2007 | Rudick et al. |
| 2007/0205221 A1 | 9/2007 | Carpenter et al. |
| 2007/0212468 A1 | 9/2007 | White et al. |
| 2008/0015494 A1 | 1/2008 | Santini et al. |
| 2008/0201241 A1* | 8/2008 | Pecoraro .......... G06Q 30/06 705/26.8 |
| 2009/0069932 A1 | 3/2009 | Rudick |
| 2009/0069933 A1* | 3/2009 | Rudick .......... B67D 1/0034 700/239 |
| 2009/0070234 A1* | 3/2009 | Peters .......... B67D 1/0041 705/26.1 |
| 2010/0031157 A1* | 2/2010 | Neer .......... G06Q 10/06 715/738 |
| 2010/0223581 A1 | 9/2010 | Manolescu et al. |
| 2011/0123688 A1 | 5/2011 | Deo et al. |
| 2011/0125334 A1 | 5/2011 | Deo et al. |
| 2011/0194295 A1 | 8/2011 | Householder et al. |
| 2012/0046785 A1 | 2/2012 | Deo et al. |
| 2012/0285986 A1 | 11/2012 | Irvin |
| 2013/0292407 A1 | 11/2013 | Beavis et al. |
| 2013/0328740 A1 | 12/2013 | Blumberg, Jr. |

FOREIGN PATENT DOCUMENTS

| | | |
|---|---|---|
| GB | 2465083 A | 5/2010 |
| JP | 2005276148 A | 10/2005 |
| JP | 2009245171 A | 10/2009 |
| JP | 5120548 B2 | 1/2013 |
| WO | 0225608 A1 | 3/2002 |
| WO | 2004069179 A2 | 8/2004 |

\* cited by examiner

BEVERAGE DISPENSING DEVICE WITH GRAPHICAL REPRESENTATION OF CUSTOMIZED BEVERAGE SELECTION

CROSS-REFERENCE TO RELATED APPLICATIONS

This application is a continuation of U.S. patent application Ser. No. 13/947,557 entitled "Beverage Dispensing Device Configured to Alter a Recipe in Response to External Inputs" and filed on Jul. 22, 2013, which is a continuation of U.S. patent application Ser. No. 12/703,003 entitled "BEVERAGE DISPENSING DEVICE" and filed on Feb. 9, 2010, which issued as U.S. Pat. No. 8,490,829 on Jul. 23, 2013 and which is a continuation-in-part of U.S. patent application Ser. No. 12/625,226 entitled "BEVERAGE DISPENSING DEVICE" and filed on Nov. 24, 2009, which issued as U.S. Pat. No. 8,335,592 on Dec. 18, 2012, each of which is hereby incorporated by reference in their entirety.

BACKGROUND

Often, at restaurants or other locations such as a consumer's residence, a beverage may be created on-demand from a mixture of ingredients. An advantage of dispensing beverages in this form is that the concentrate containers and water supply typically occupy significantly less space than is otherwise required to store the same volume of beverage in individual containers. Moreover, this dispensing equipment likewise eliminates increased waste formed by the empty individual containers as well as additional transport costs. These and other technological advances have allowed food and beverage vendors to offer more diverse choices to consumers.

Beverages that confer health benefits are increasingly gaining popularity. Such beverages may restore or provide hydration, vitamins, energy, or other ingredient(s) to provide a health benefit. These beverages are now offered in several personalized variations. For example, Gatorade®, commercially available from PepsiCo, has been expanded to include additional flavors, and is also now offered in a reduced calorie version, commercially available as G2®. Furthermore, non-caloric "fitness" beverages, such as Propel®, are also commercially available in different flavors.

The current diverse offerings for such beverages has allowed more individuals to enjoy the benefits of these beverages, however, the formulation of several current beverages is often based on generalizations and still forces consumers to determine which product will benefit them. For example, a consumer may believe that a reduced calorie beverage may assist in weight loss, however, that specific beverage may not be sufficient to sustain the consumer during their aggressive routine work-out, and/or may not provide enough hydration. Furthermore, depending on age, sex, weight, and other individual differences, one person may deplete their store of certain electrolytes faster than other electrolytes. Therefore, providing a beverage having predefined amounts of several electrolytes or ingredients, may lead to the individual having too much of one electrolyte while being deficient in another.

Certain prior art systems attempt to remedy these deficiencies by asking user's to provide demographic and personal information. Unfortunately, however, such systems are prone to data entry errors, as well as forcing users to guess certain parameters. Furthermore, a common goal for most athletic individuals is to either lose weight or ensure any weight gain is muscle mass. Thus, reliance on individuals to correctly provide data to personal questions is prone to error. Other systems attempt to base beverage recommendations on genetic data, however, such systems require invasive procedures and the threat of genetic information being spread to those with little regard to its privacy.

Further systems may provide methods for collecting data to personalize beverages, however, such systems generally require users to travel to a secondary location, such as a doctor's office or laboratory to accurately measure individual parameters. Often, these parameters have changed by the time of testing. Furthermore, increased costs associated with multiple sensors, frustration of wearing or locating multiple physiological measuring devices, and/or inaccurate assessment of the user's exertion level may contribute to poor adoption of certain systems. Therefore, improved systems and methods relating to the dispensing of beverages would be desirable.

SUMMARY

Aspects of this disclosure relate to novel methods for dispensing a composition, such as a beverage. Certain aspects relate to beverage dispensers that receive measurements of a physiological parameter regarding a user. In one embodiment, a beverage dispenser may formulate at least one beverage recipe in response to the measured parameters. The beverage dispenser may have a wireless transceiver configured to receive data from a biosensor that measures a physiological parameter of a user. The dispenser may also have a user input device to receive an input directing the discharge of a first recipe from the apparatus. In one embodiment, the user input device may include a touch screen. The touch screen may also display one or more options to a user. The user input device may also allow the user to select a class of beverages, a specific beverage, or combinations thereof.

In one embodiment, physiological measurements from a biosensor may received at the beverage dispenser and used to in conjunction with dispensing a beverage. Measured physiological parameters, user inputs, or combinations thereof may be used to dispense a non-requested recipe. The biosensor may be dispensed from the beverage dispenser. In other embodiments, a biosensor may be associated with a beverage receptacle, such as being integral or removable from the lid, cap, neck, or body portion of any can, bottle, cup, or container.

In one embodiment, the user input device is operable to select a class of beverages. In one embodiment, the class of beverages may contain one or more branded beverages. Data from the biosensor may be used to modify the recipe of the beverage based upon measured physiological parameters. In another embodiment, the user input selects a specific beverage recipe. Data from the biosensor may be used to alter the recipe to another existing beverage or a custom beverage. In certain embodiments, non-physiological data may also be considered. In one embodiment, environmental and/or biographical data may be utilized in any determination. In another embodiment, exertion data may be calculated. The calculation of exertion data may receive inputs regarding at least one physiological parameter (but may also include inputs from one ore more non-physiological parameters) to derive a second physiological parameter not being measured. Such calculation may be beneficial to reduce costs associated with multiple sensors, reduce frustration of wearing or locating multiple physiological measuring devices, and/or allow more accurate assessment of the user's exertion level. In one embodiment, the exertion data may be calculated at the beverage dispenser.

Further aspects of the invention relate to dispensing ingredients of a beverage in accurate quantities. In one embodiment, sensors measure several parameters of an ingredient being dispensed. Based upon the results, the amount of another ingredient may be adjusted. In certain embodiments, the dispensed beverage has one or more micro ingredients. In one embodiment, a micro ingredient may include: sodium chloride, sodium citrate, mono-potassium phosphate, quercetin, and combinations thereof. In one embodiment, at least two micro ingredients are dispensed from a micro dosing module with variable viscosity capabilities.

In certain embodiments, one or more novel methods may be conducted with a computer-readable medium having computer-executable instructions that may be executed by a processor to perform the methods. In one embodiment, a computer-implemented method may receive a user input configured to select a beverage formulation. In one embodiment, the beverage formulation may be a commercially available branded beverage. The beverage may be a hydration beverage, energy drink, juice, water, diary product, and combinations thereof. According to various aspects, one or more dispensing systems may be operatively connected to memory modules that store one or more recipes for the beverage formulation(s). The memory modules may be remotely located on a communication network.

Certain embodiments receive one or more inputs from a biosensor, either alone or in combinations with user inputs, at a beverage dispensing device. The inputs may be utilized at the beverage dispenser to modify a concentration of an ingredient of a beverage formulation. Any ingredient within the recipe is within the scope of this disclosure. One or more beverage dispensing systems may be in operative communication with a display device and/or a communication network. In one embodiment, multiple dispensing systems are connected to a communication network, such as the Internet or an intranet. In one embodiment, several dispensing systems may be connected to a central server. In one embodiment, several dispensing systems may be in direct communication with each other. In certain embodiments, a dispensing system may include a beverage dispensing head through which multiple beverage-forming liquids can be discharged. In certain embodiments, a dispensing system may simultaneously discharge a plurality of different ingredients, such as non-carbonated and carbonated water or different blends of flavorings, such as concentrates. In one embodiment, a dispensing system is configured to discharge several different beverages from a single nozzle. In certain embodiments, a dispensing system may supply beverages formed from combinations of one or more different liquids without having to extensively reconfigure the system's internal fluid supply lines and/or electronic circuitry.

One or more of the beverage formulation recipes may be stored on a computer-readable medium, either locally or remotely. For example, in one embodiment, the recipe of a branded beverage, and/or a modified beverage may be stored. Further embodiments may store the recipe of the beverage that was dispensed by the beverage dispensing system. The storage of recipes of any beverage formulation, including unique formulations created by one or more consumers, is within the scope of this disclosure.

DETAILED DESCRIPTION

Figure 1:
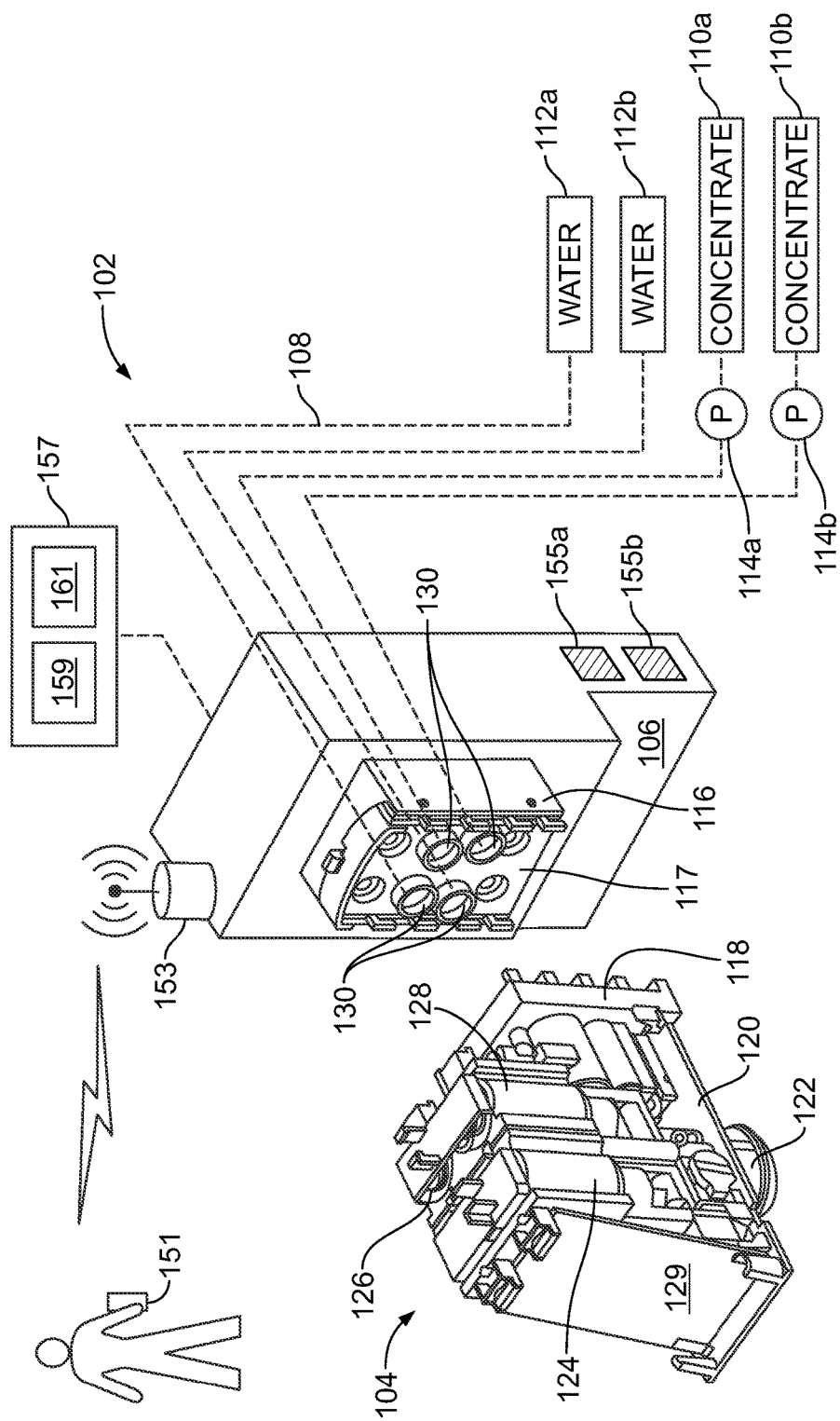
FIG. 1 is an exploded view and schematic diagram of an exemplary dispensing system and dispensing head in accordance with one embodiment of this invention.

FIG. 1 illustrates an exemplary dispensing system 102 that may be configured to dispense a beverage comprising a plurality of ingredients. While the exemplary dispensing system 102 will be described in the context of dispensing a beverage, those skilled in the art will appreciate that other compositions, such as medicaments, lotions, supplements, condiments, may be dispensed according to the teachings of this disclosure. Looking to FIG. 1, the exemplary dispensing system 102 includes a dispensing head 104, and a counter-located base 106, to which the dispensing head 104 may be removably mounted. Reservoirs 110a and 110b may store ingredients configured to be dispensed from dispensing system 102, such as flavored concentrates that may be in different forms, such as liquids (including syrups) or powders. Pumps 114a and 114b may be connected to reservoir 110a and 110b, respectively. The pumps 114a and 114b allow the movement of the associated ingredient through base 106 and into the dispensing head 104. A portion of the ingredients may comprise water (for example, see elements 112a and 112b). In one embodiment, one water source may supply a noncarbonated water stream. The second source may include a carbonator (not illustrated) that supplies carbon dioxide to the water stream it supplies through base 106 into the dispensing head 104. In another embodiment, the water source may be substantially devoid of carbonation. In yet other embodiments, a plurality of water sources may be configured to provide different levels of carbonated water.

The tubing 108 through which the four illustrated fluid streams flow into the base 106 may terminate at mounting block 116. As seen in FIG. 1, mounting block 116 may be removably mounted to the dispensing head 104. In the illustrative embodiments, mounting block 116 may have a front face 117 comprising passageways 130 to one or more reservoirs for one or more ingredients such as concentrate 110a/110b and/or water 112a/112b. The passageways 130 may be integrally formed with and extend from the block front face 117. The front face 117 and/or another portion of the mounting block 116 may further comprise a locking mechanism for aligning and ensuring proper fitting between the passageways 130 and the dispensing head 104.

The illustrated dispensing head 104 includes a vertical back plate 118 from which a base plate 120 extends horizontally. Back plate 118 may be removably coupled to dispensing unit mounting block 116 and a valve body may be seated on the base plate 120. A nozzle assembly 122 is shown to extend below the base plate 120. Valve body may comprise a plurality of conduits through which the ingredients flow into nozzle assembly 122. One or more valve units may be mounted to the valve body. For example, valve units 124, 126, 128 may regulate the flow of a separate one of the fluid streams through the dispensing head 104 and out of the nozzle assembly 122.

The dispensing system 102 may comprise a controller 127 (FIG. 2) that includes one or more computer-readable mediums, such as circuit board 129. Circuit board 129 is shown mounted to the base plate 120 and may comprise the electrical components (not illustrated) that are used to regulate the actuation of pumps 114a and 114b and/or valve units 124, 126, 128. Circuit board 129 may also comprise computer-readable instructions that when executed by a processor, such as processor (such as processor 206, described in more detail below in relation to FIG. 2) to provide energization signals to valve units 124, 126, 128, control signals to the pumps 114a and 114b, and/or feedback signals from the dispensing head 104 to the dispensing system 102. The beverage dispensing system 102 may have a wireless transceiver 153 configured to receive data from a biosensor 151 that measures a physiological parameter of a user.

Historically, electronic circuitry 129 (or another component comprising a computer-readable medium), comprised a "flavor chips." The flavor chip comprised computer-executable instructions, that when executed by a processor, would execute a method for mixing a predefined beverage. Unfortunately, past flavor chip technology had to be adapted to the mechanical properties of each dispenser and each flavored beverage required a separate flavor chip. Thus, in certain prior art systems, changing beverages to be dispensed from a dispenser would require the new flavors to be "mapped" onto the chip. For example, each parameter had to be adjusted to ensure the dispensed beverage received the intended proportions of ingredients. Aspects of the invention relate to systems and methods for dispensing custom beverages that do not require the inconvenience of mapping of different flavor chips for each possible combination of the various ingredients.

While FIG. 1 shows one exemplary dispensing system 102, those skilled in the art will readily appreciate that other systems that are either configured or able to be modified to dispense a multi-ingredient beverage according to one or more teachings of this disclosure are within the scope of the invention. Further exemplary systems, including exemplary heads and/or nozzles that may be selectively combined are disclosed in Assignee's U.S. patent application Ser. No. 10/412,681, BEVERAGE FORMING AND DISPENSING SYSTEM, filed Apr. 14, 2003, U.S. Patent Pub. No. 2004/0084475 A1, published May 6, 2004, and/or U.S. patent application Ser. No. 11/118,535, BEVERAGE DISPENSING SYSTEM WITH A HEAD CAPABLE OF DISPENSING PLURAL DIFFERENT BEVERAGES, filed Apr. 29, 2005, U.S. Pat. Pub. No. 2006/0097009, which are incorporated herein by reference in their entirety for any and all purposes.

Figure 2:
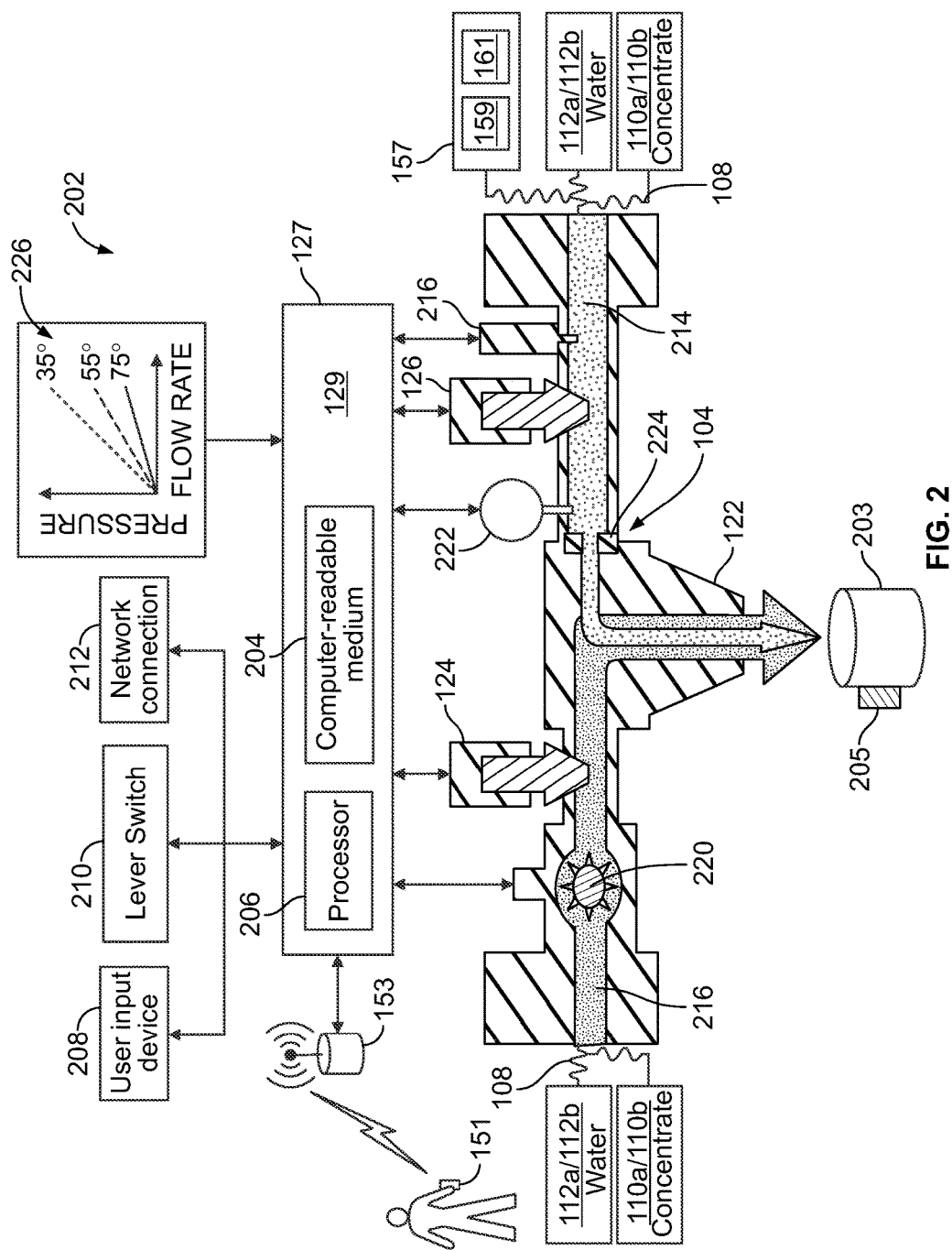
FIG. 2 shows an exemplary embodiment of one dispensing system in accordance with one embodiment of the invention.

FIG. 2 shows an exemplary dispensing system 202 that may be configured for use without prior art flavor chips to dispense custom beverages. Dispensing system 202 may be configured to implement novel methods, such as the methods shown in the flowchart of FIG. 3. In this regard, certain novel features of dispensing system 202 will be described in relation to the methods of FIG. 3, however, the novel apparatus shown in FIG. 2 is not limited to only these methods but are merely provided to demonstrate exemplary uses of dispensing system 202. As seen in FIG. 2, dispensing system 202 comprises a controller 127 that includes an electronic circuitry 129, which may be identical or similar to electronic circuitry 129 shown in FIG. 1. Electronic circuitry 129 comprises a computer-readable medium 204 which may be magnetic, digital, optical, or any format configurable to comprise computer-executable instructions that may be executed by a processor, such as processor 206.

Processor 206 may be configured to execute instructions on the computer-readable medium, such as computer-readable medium 204, received from a user input device 208, lever switch 210 and/or a network connection 212. The user input device 208 may include any components or group of components (including a switch similar or identical to lever switch 210) that allows a user to provide an input to dispensing system 202, which may be mechanical, electrical, or electromechanical. Novel uses of user input device 208 may be implemented in accordance with one or more novel methods described herein. As one example, user input device 208 may be used in conjunction with step 302 shown in FIG. 3. At step 302, instructions may be received for dispensing a beverage. In one embodiment, user input device 208 may allow a user to instruct dispensing system 202 to dispense a specific beverage formula. In one embodiment, user input device 208 may comprise a touch screen that is in operative communication with electronic circuitry 129. The touch screen may be configured to display a plurality of beverage classes. For example, in one embodiment, the classes may include, but are not limited to: colas, diet colas, energy drinks, water, fruit juices and combinations of any of these groups. In certain embodiments, a user may be able to pick a beverage class from a group of classes. In various embodiments, the display of possible beverage for selection may be adjusted based upon the levels or presence of specific ingredients detected in dispensing system 202.

The touch screen may be configured to allow a user to first select a specific brand of beverage, such as a particular energy drink from a plurality of energy drinks. Still yet, the touch screen may allow a user to pick a specific commercially available beverage and further refine the ingredients to be dispensed to form a similar beverage. In one embodiment, the refined beverage has the same ingredients, however, comprises different proportions or amounts of the ingredients. For example, a user may first select the cola beverage "Pepsi," and then wish to adjust one or more parameters of the Pepsi to be dispensed. For example, the user may wish to adjust the sugar content and/or carbonation of the beverage to be dispensed. In another embodiment, the refined beverage has at least one different ingredient, for example; at least a portion of the high fructose corn syrup may be replaced with various levels of one or more ingredients.

While the exemplary embodiment was described in relation to a touch screen, other input devices may be used in combination with or in lieu of a touch screen. For example, a user may swipe a card having electronic information a sensor, such as for example, an optical, magnetic, or RFID sensor to provide a user input. In another embodiment, the user may utilize a biometric input to provide an input. Yet in other embodiments, the user may enter alphanumeric inputs using a keyboard. The lever switch 210 may also be operatively connected to electronic circuitry 129 to provide an input indicative that a receptacle is placed under the nozzle 122.

Network connection 212 may also provide one or more user inputs (as well as transmit outgoing signals) coupling dispensing system 202 to a communication network, such as a LAN or the Internet. The dispensing system 202 (and other devices) may be connected to a communication network via twisted pair wires, coaxial cable, fiber optics or other media. Alternatively, radio waves may be used to connect one or more beverage dispenser systems to the communication network. In one such embodiment, one or more dispensing systems may be in communication with each other and readily transmit and receive information regarding other dispenser systems, including a unique formula dispensed to a particular user. In one embodiment, a plurality of dispensing systems may each be coupled to each other through a central server. Yet in another embodiment, the dispensing systems may communication directly with each other. Thus, in one or more embodiments, electronic circuitry 129 may include computer-executable instructions for transmitting information to other dispensers and/or a server.

Figure 3:
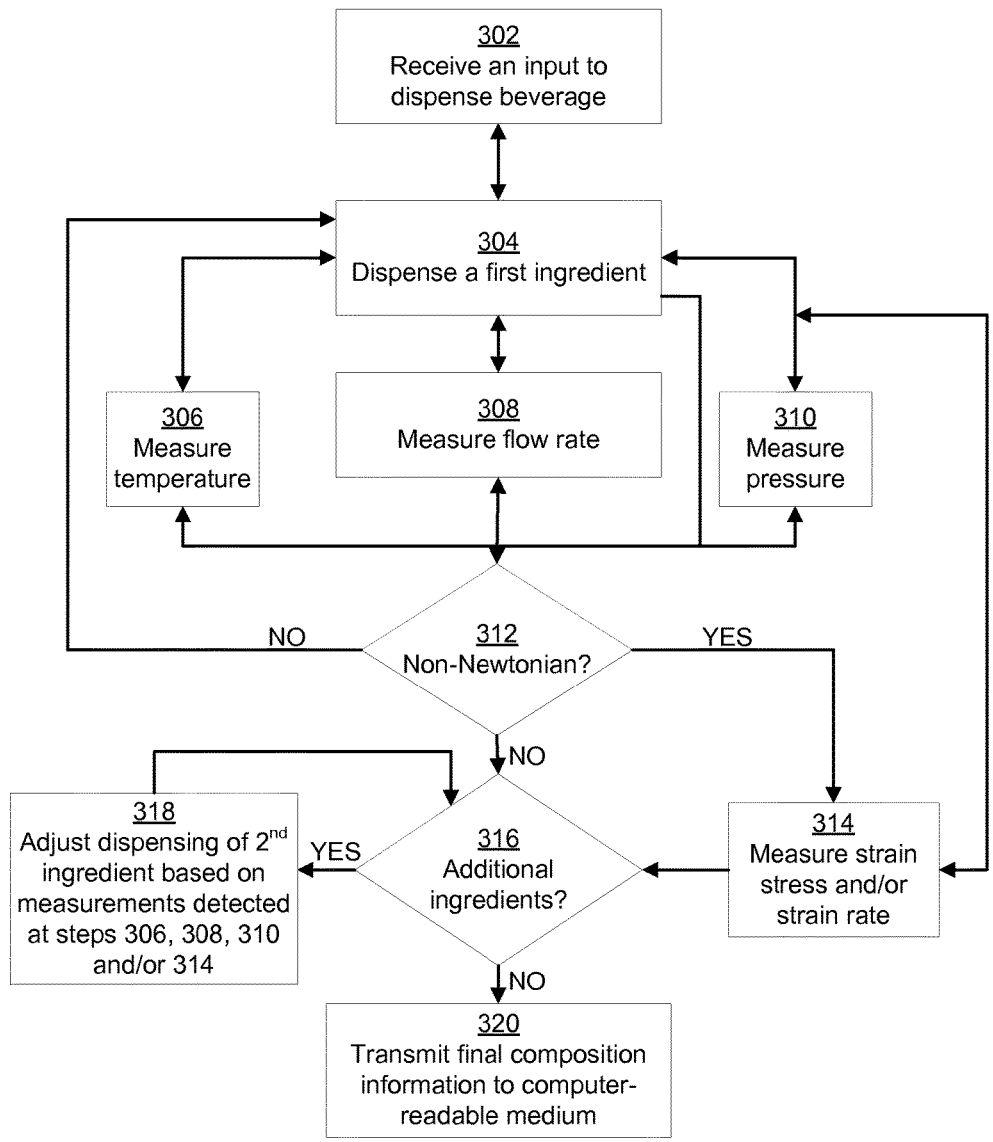
FIG. 3 is a flowchart of an exemplary method in accordance with one embodiment of the invention.

Step 304 of FIG. 3 may be implemented to dispense a first ingredient into a conduit of the dispensing system 202. Looking to the exemplary dispensing system 202 in FIG. 2, a first conduit, such as conduit 214 may also be connected (for example, through a series of valves and/or through tubing 108) to a beverage ingredient source (such, as for example concentrate(s) 110a/110b). During beverage preparation and dispensing, one or more ingredients, such as water 112a/112b and/or concentrates 110a/110b may pass through the first conduit 214. Conduit 214 is merely exemplary, as additional or fewer ingredient sources may be upstream or downstream from conduit 214. Moreover, dispensing system 202 may comprise a plurality of conduits, such as second conduit 216. The second conduit 216 may be in connection with one or more ingredient source, such as water 112a/112b and/or concentrates 110a/110b. In the illustrative dispensing system 202, the first conduit 214 and the second conduit 216 diverge at the nozzle 122, where ingredients may be mixed and dispensed from the dispensing system 202.

Regarding the nozzle 122, the illustrated dispensing system 202 of this invention may includes the single dispensing head 104 (shown in FIGS. 1 and 2) with plural passageways, such as conduits 214, 216 (shown in FIG. 2) through which concentrated ingredients may flow. Valve units 124, 126, and 128 may operate independently from each other and be independently controlled. Thus, the disclosed systems 102, 202 may be constructed so that a single dispensing head 104 may be used to discharge beverages blended from any one of two or more distinct ingredients (such as concentrates) to a single nozzle 122. In certain embodiments, this may eliminate the need to provide the system 102 with multiple dispensing heads wherein each head is employed to dispense a single beverage. Other embodiments, however, may implement a plurality or heads and/or nozzles. Regardless of the quantity of nozzles utilized, those skilled in the art will appreciate that valves 124 and 126 may be simultaneously opened to discharge a beverage that is a desirable mixed blend of two or more concentrates or other ingredients.

Dispensing head 104 may be further designed so that the passage of one or more ingredients comprising carbonated water is discharged has a tapered increase in cross-sectional area along its length as measured starting from the top to the bottom. That is, a conduit or passage within dispensing system may be narrow at the high pressure end and widens considerably, to as much as ten times its width at the low pressure end. Consequently, as the water and gas fluid stream flows through a tapered passage, the pressure of the gas bubbles in the stream may decrease continually but gradually. This gradual decrease in pressure reduces the extent the carbon dioxide, upon the discharge an outlet breaks out of the fluid stream. The reduction of carbonation breakout serves to ensure that the blended beverage has sufficient gaseous-state carbon dioxide to impart a desirable taste.

Conduits 214, 216 may comprise a plurality of sensors to measure one or more parameters of one or more ingredients that travel through the respective conduit 214, 216 to the nozzle 122. The measured parameters of a first ingredient may be used to adjust the amount or parameter of a second ingredient to be dispensed. Yet in other embodiments, the measured parameters of the first ingredient may be used to dispense the amount of that ingredient being dispensed. In certain embodiments, several parameters may be measured within conduit 214 and/or conduit 216. In one embodiment, steps 306, 308, and/or 310 may be implemented to measure the temperature, viscosity, pH, flow rate, and/or pressure of a first ingredient in the first conduit. In one embodiment, step 306 may comprise the implementation of temperature sensor 218 (shown in conduit 214), step 308 may include measurements with flow rate sensor 220 (shown in conduit 216) and step 310 may comprise measurements from PSI meter 222 (shown in conduit 214). While, the sensors are shown in two different conduits (214, 216), those skilled in the art will appreciate that both (and additional) conduits may have each of the above-described sensors as well as additional sensors.

Step 312 may also be implemented to determine if the ingredient (or one of the ingredients) is a non-Newtonian fluid. This determination may be based one or more measurements of steps 308-310 and/or based upon known information regarding the ingredient. For example, an electronic signal may be transmitted from the electronic circuitry 129 that is indicative that the ingredient(s) in at least one conduit 214, 216 is/are non-Newtonian. If at step 312, it is determined that the ingredient is non-Newtonian, step 314 may be implemented. At step 314, one or more sensors may detect or otherwise measure the shear stress and/or strain rate of the ingredient(s). In one embodiment, a first sensor in a first conduit 214 may be used to detect the flow rate of a first fluid; however, a second sensor in the same first conduct 214 may be used to detect the flow rate of a second fluid.

In those embodiments, where the ingredient is non-Newtonian, the shear stress could utilize sensors to first measure the gradient of for example, by using a first sensor to measure the gradient of the velocity profile at the walls of the conduit 214, 216. Computer-executable instructions on computer-readable medium 204 may use processor 206 to multiply the signal from the first sensor by the dynamic viscosity to provide the shear stress of that particular ingredient or combination of ingredients. In one embodiment, one or more micro-pillar shear-stress sensors may be used in conduit(s) 214, 216. The micro-pillar structures may be configured to flex in response to the drag forces in close proximity to the outer perimeter of the conduit(s) 214, 216 (i.e., the walls). The flexing may be detected electronically, mechanically, or optically. The result of the flexing may be received as an electronic signal by computer-executable instructions on computer-readable medium 204. Processor 206 may utilize the received electronic signal to determine wall-shear stress. As discussed above, one or more of the conduits 214, 216 may comprise a temperature sensor 218, which may transmit electronic signals as an input to electronic circuitry 129. The input from temperature sensor 218 may also be used in conjunction with one or more other sensors to determine the viscosity of an ingredient of composition comprising a plurality of ingredients.

Further aspects of the invention relate to novel uses of adjustable orifices. For example, in certain embodiments, rather than implement the volumetric measurement then dispensing of ingredients, adjustable orifices may be used to simultaneously measure and dispense ingredients. For example, as an ingredient (or compositions having a plurality of ingredients) flows through a conduit, flow meter 220 and temperature sensor 218 may determine the viscosity of the ingredient. Based upon the parameters detected by sensor 218 and meter 220, information may be received from the electronic circuitry 129 that adjusts, rather than merely opening or closing, an orifice (see, e.g., elements 126 and 224 within conduit 214). In certain embodiments, this may result in a more homogeneous combination of the ingredients. In other embodiments, it may result in less wear and tear on the dispensing device 202. In yet further embodiments, it may result in more efficient measurements of ingredients. Obtaining accurate measurements of ingredients may be of special importance, for example, when dealing with micro-nutrients, such as nutrients that comprise less than about 5% of the entire beverage or composition. In certain embodiments, a first ingredient may be dispensed from dispensing system 202 or at about 6% of the final beverage.

In one embodiment, the flow rate of at least one ingredient may be adjusted by the same mechanism that measures the flow rate. For example, exemplary flow rate sensor 220 (shown in conduit 216 of FIG. 2) may comprise a turbine or a paddle meter that is configured to measure the flow rate of an ingredient within conduit 216 (this measurement may be conducted in cooperation with information received from one or more other sensors within dispensing device 202). Based upon the determination of the flow rate, electronic circuitry 129 may transmit a signal that causes a drag placed upon at least a portion of sensor 220 (such as a turbine or paddle portion) thus acting as a restrictive orifice, such that the quantity of ingredient that is dispensed through conduit over a predetermined period of time is reduced. Likewise, electronic circuitry 129 may transmit a signal that causes less drag placed upon at least a portion of sensor 220, (i.e., at least a turbine or paddle), thus acting to increase the quantity of ingredient that is dispensed through conduit over a predetermined period of time is reduced. This may occur during or before step 316, in which it is determined whether further ingredients are to be dispensed. In further embodiments, one or more parameters of any ingredient being dispensed may be adjusted based upon information received from one or more sensors (such as sensors 218 and/220). For example, the carbonation levels of the ingredient may be altered to adjust the viscosity of the ingredient being dispensed.

Further, in the preparation of certain compositions to be dispensed, it may not be desirable to dispense a first ingredient under the same pressure as a second ingredient (for example, when dispensing a second ingredient at step 318). In some instances, it may be desirable to reduce the pressure under which a first ingredient is dispensed, in yet other embodiments; it may desirable to increase the pressure that an ingredient is dispensed, for example, to ensure proper mixing or the intended profile of the beverage. In certain embodiments, adjustable orifices may be implemented to ensure the optimal flow rate is implemented for certain ingredients. For example, computer-readable instructions may be used to achieve the optimal combination of pressure and flow rate of an ingredient passing through a conduit 214, 216, such as by use of an adjustable orifice. A simplified graphical illustration is shown by way of element 226. As seen by element 226, adjusting an input, such as through a step motor (for example "35°", "55°", or "75°") may be used to obtain a preferred combination of flow rate and pressure. Those skilled in the art will readily appreciate that element 226 is merely illustrative and that other implementations, including the use of more than three adjustable settings, are within the scope of this disclosure.

At step 320, information regarding the dispensed beverage or composition may be stored on a computer-readable medium, such as computer-readable medium 204. The computer-readable medium of step 320 is not, however, required to be within or local to the dispensing system 202. Instead, the information regarding the dispensed beverage may be transmitted through network connection 212 to a remote computer-readable medium. In one embodiment, the unique composition dispensed through the implementation of one or more methods shown in FIG. 3 may be received at a second dispensing system, which may dispense the substantially the same beverage or composition.

Figure 4:
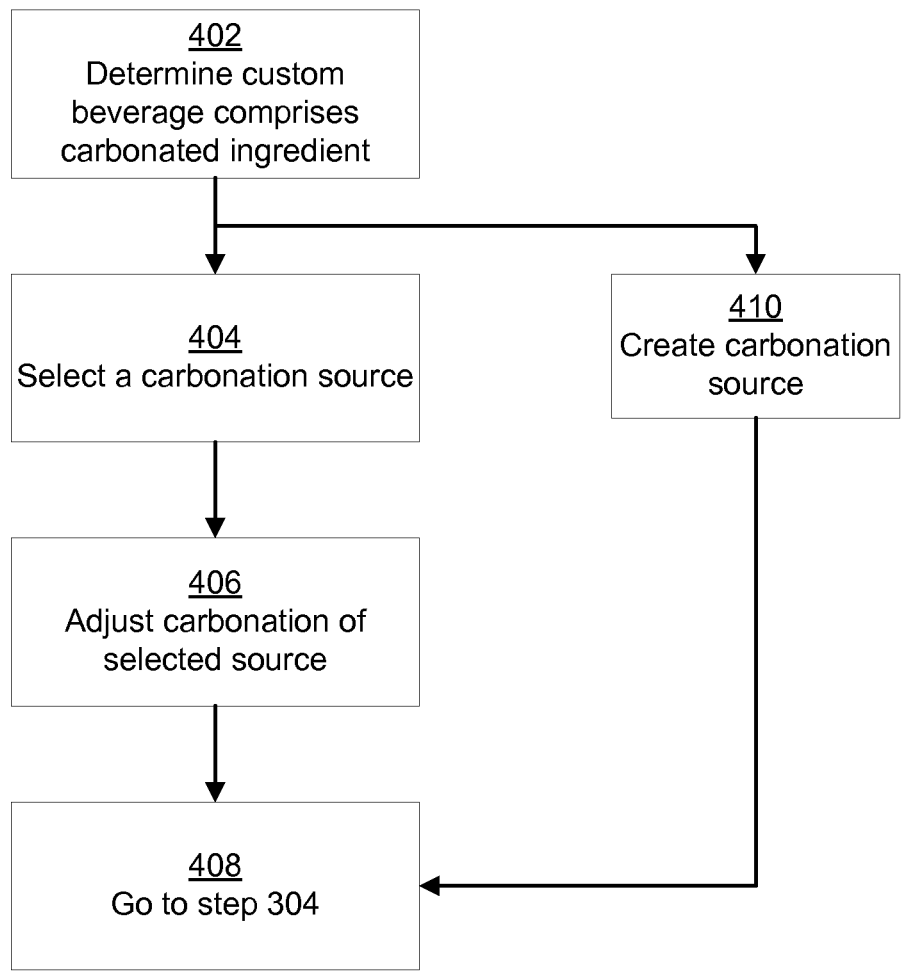
FIG. 4 is a flowchart of an exemplary method in accordance with one embodiment of the invention.

FIG. 4 shows a flowchart of an exemplary method in accordance with one embodiment of the invention. At step 402, it may be determined whether a custom beverage comprises a carbonated ingredient, such as carbonated water. In one embodiment, steps 404 and/or 406 may be performed to select a carbonation source (step 404) and adjust the carbonation of the selected source (step 406). For example, at step 404, it may be determined that the beverage requested contained carbonated water, however, the user requested that the beverage comprise less high fructose corn syrup, therefore the carbonation levels of the beverage may be reduced. Exemplary embodiments are disclosed later in this disclosure, for example, in reference to FIGS. 5-6. In one embodiment, the level of carbonation (or any gas) of a second ingredient is adjusted based upon electronic signals received from one or more signals regarding measurements from sensors measuring parameters of a first ingredient. Such parameters may be the flow rate, viscosity, pH, pressure, level of carbonation, level of constituents, such as sugar, water, coloring, etc., and/or any combination of these and other parameters that relate to the first ingredient.

In certain embodiments, the carbonation source selected in 404 may be one of a plurality of sources. For example, different sources may comprise various levels of carbonation; therefore, one source comprising the closest amount of carbonation needed may be selected before adjustment. In certain embodiments, dispensing system 102, 202 may selectively discharge streams of carbonized and non-carbonized water from separate containers, for example, reservoirs 112*a*-112*b*. Therefore, in certain implementations, the dispensing head 104 can be employed to dispense beverages selectively made from either carbonized or non-carbonated water. Alternatively, the dispensing head 104 may be used to dispense a beverage comprising carbonated water and non-carbonated water. In one embodiment, adjustable orifices are opened simultaneously to cause the simultaneous dispensing of both carbonated and non-carbonated water. This is useful when it is desired to blend these two liquids with a concentrate to produce a lightly carbonated beverage. In one embodiment, by varying the amount of time each orifice is open at one or more predetermined diameters, the extent to which the water supplied for the beverage may be set anywhere between fully carbonated (100% carbonated water supply) to no carbonation (100% non-carbonated water supply).

In yet other embodiments, step 410 may be used to create a carbonation source. In one embodiment, a first conduit such as conduit 214 may comprise water and conduit 216 may comprise carbon dioxide gas. Thus, based upon the sensors 218, 220, 222, and/or other sensors within conduits 214, 216 or elsewhere within dispensing system 202, the amount of water that is combined with the carbon dioxide gas is determined and dispensed, such as through an adjustable orifice. Regardless of whether steps 404 and 406 or step 410 is implemented, step 408 may be initiated. In one embodiment, the resultant carbonated ingredient may be dispensed into a conduit, such as conduits 214 and/or 216. (see, e.g., step 304 of FIG. 3).

It should further be appreciated that not embodiments have all of the above-described features and/or include each step and/or process of the disclosed methods. For example, certain embodiments may be provided with different quantities of fluid passageways and valve units than have been described above with respect to the illustrated embodiments. It is anticipated that these alternative embodiments of the invention may be used to provide a means for forming a beverage from a combination of a plurality of ingredients, which may be discharged from a either a plurality of nozzles or, alternatively, a single nozzle. Moreover, one or more nozzles may be configured to provide a discharge passage that extends vertically downward. Yet in other embodiments, one or more discharge passages for ingredients may have a spiral or helical configuration. While the exemplary dispensing system 102 shown in FIG. 1 may be used in a commercial setting, for example, a restaurant, those skilled in the art will readily appreciate that the teachings of this disclosure may be applied to any dispensing system, such as implemented in bar gun technology and/or residential use. Further, embodiments within the scope of this disclosure may be used with frozen beverages and/or non-carbonated beverages.

Further aspects of the invention relate to systems and methods that allow consumers to adjust one or more ingredients of a beverage formulation recipe. For example, consumers often enjoy beverages that, in addition to a base flavor, include a supplemental flavor, such as cherry or lemon-lime. Yet consumers are increasingly interested in adjusting one or more ingredients in their beverages, such as the amount of sugars, often in the form of high fructose corn syrup (HFCS). As companies attempt to expand to meet the personalized needs of their consumers they may risk changing the very taste profile that the consumer enjoys, and/or increased costs manufacturing and transporting multiple variations of the same branded beverage.

Figure 5:
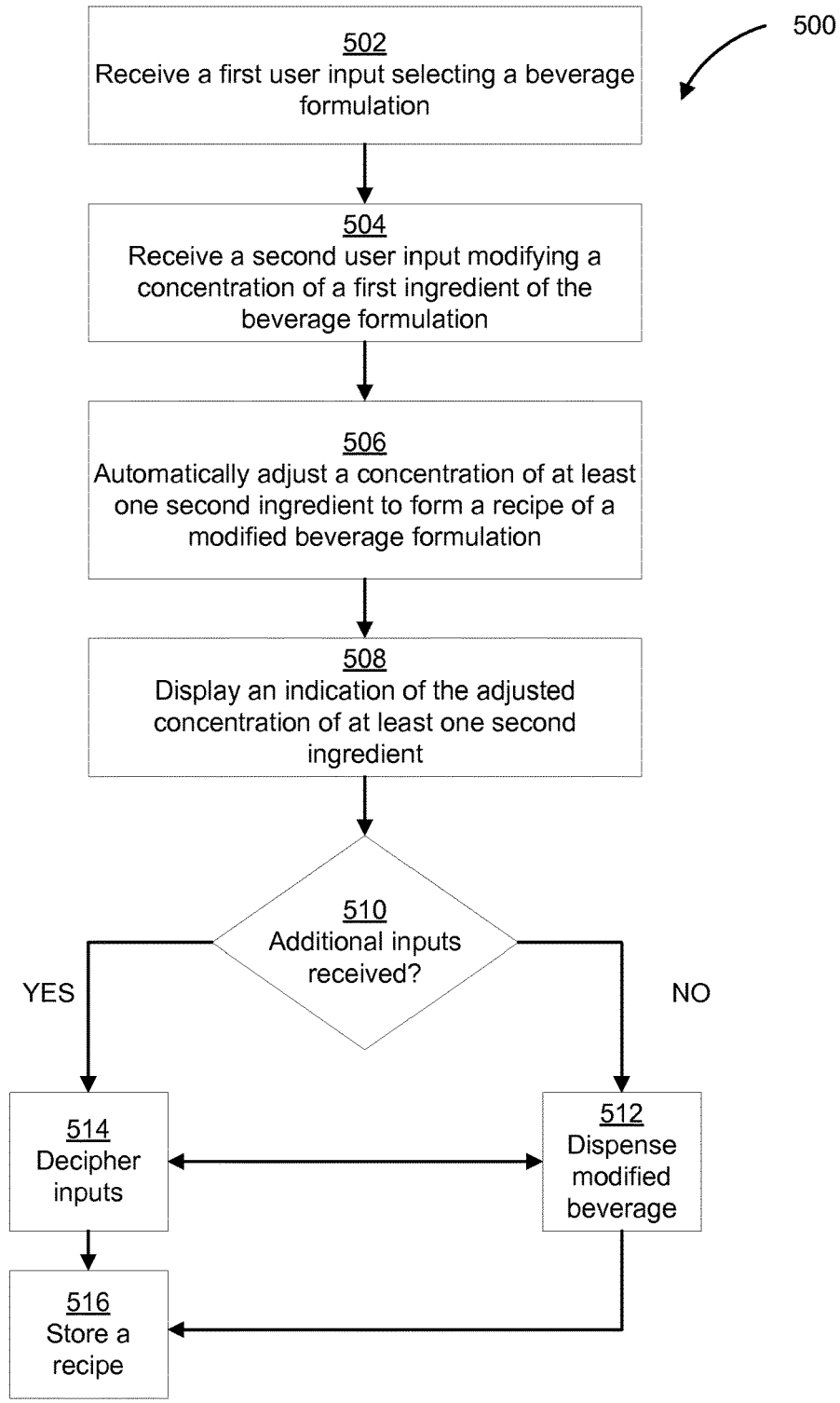
FIG. 5 is a flowchart of an exemplary method in accordance with one embodiment of the invention.

In certain embodiments, a consumer may adjust the amount (concentration) of one or more ingredients, such as a sweetener, of a beverage formulation. Based upon the consumer's adjustment, one or more additional ingredients may be automatically adjusted. FIG. 5 is a flowchart of an exemplary method 500 according to one embodiment of the invention. To provide the reader with a clear understanding of certain embodiments of the invention, exemplary methods will be described in relation to the exemplary beverage dispensing systems depicted in FIGS. 1 and 2, however, those skilled in the art with the benefit of this disclosure will readily appreciate that other dispensing apparatuses can perform (or may be modified to perform) the methods disclosed herein without undo experimentation. In accordance with one embodiment, a first user input may be received at a processor in communication with a memory storing one or more recipes of beverage formulations (see 302 of FIG. 3). In one embodiment, the first user input may be received at beverage dispensing system 102 and/or 202. The first user input may select a beverage formulation recipe from a plurality of beverage formulation recipes. For example, in one embodiment, user input device 208 (shown in FIG. 2) may allow a user to select a specific beverage formula. In one embodiment, user input device (such as input device 208) may comprise a touch screen that is in operative communication with electronic circuitry 129. Electronic circuitry 129 includes computer-readable medium 204 which may store one or more recipes for beverage formulations. As explained in more detail below, the recipes (either stored in medium 204 or another medium) may be modified beverage formulations created by one or more consumers.

A display device may be configured to display a plurality of beverage classes to a consumer. For example, a display device may be operatively connected to beverage dispensing system(s) 102 and/or 202. In other embodiments, the beverage dispensing system(s) 102 and/or 202 may be configured to transmit an electronic signal through network connection 212 to be received at a remote display device. In one embodiment, the remote display device may be operatively connected to a consumer's personal computer (PC), mobile device, including a mobile phone, or any electronic device.

Figure 6:
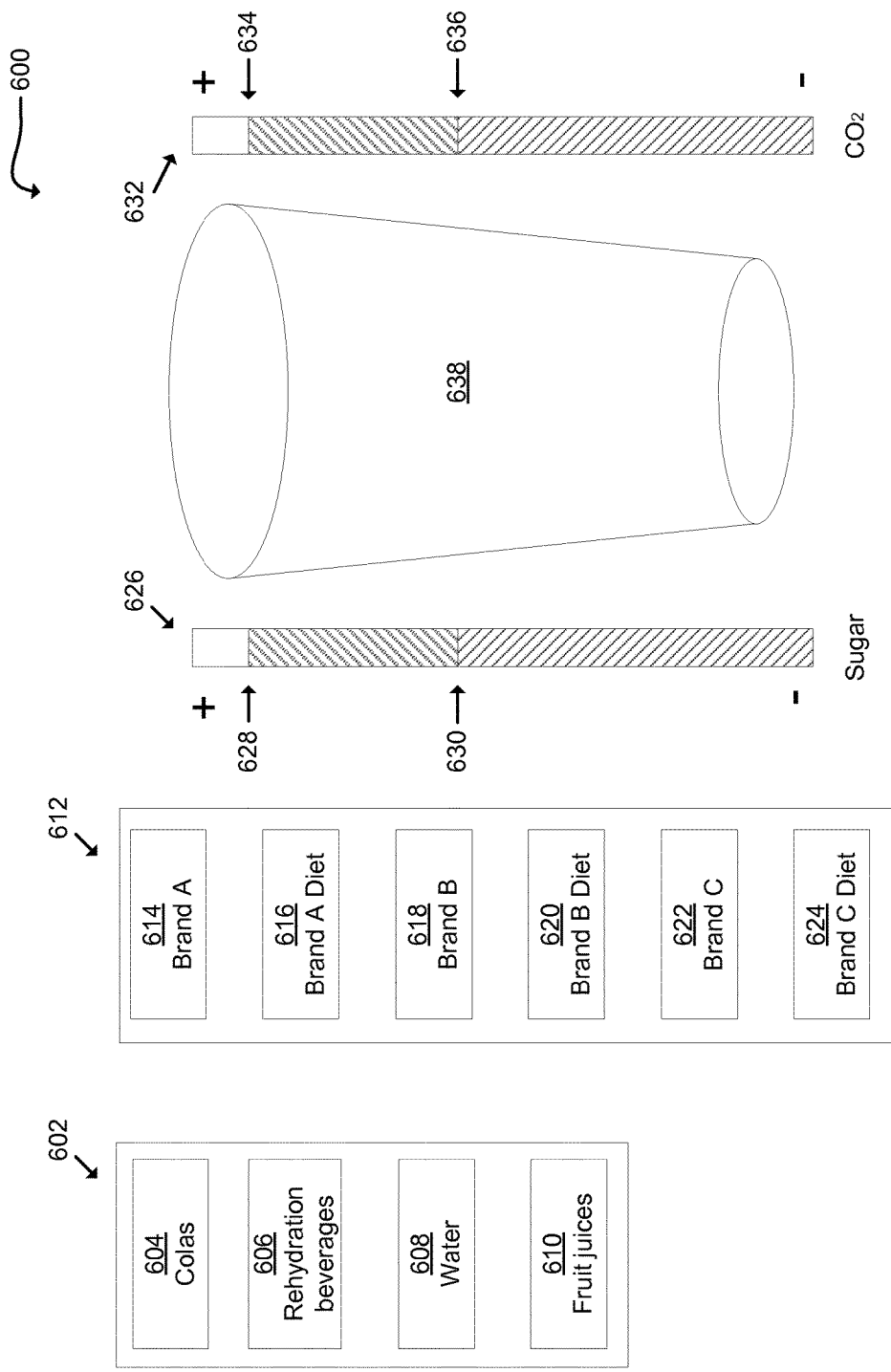
FIG. 6 is an exemplary graphical user interface in accordance with one embodiment of the invention.

FIG. 6 shows an exemplary graphical user interface 600 that may be generated from electronic signals transmitted in accordance to one or more embodiments of this disclosure. As seen in FIG. 6, a group of classes 602 may be displayed to the consumer. Exemplary classes of beverages 602 may include, but are not limited to: colas 604, rehydration beverages 606, water 608, and/or fruit juices 610. Those skilled in the art with the benefit of this disclosure will readily appreciate that these categories are merely exemplary and other categories may include one or more of the same beverage options. In certain embodiments, a consumer may be able to provide one or more user inputs that determine what beverages are grouped into one or more classes. In one embodiment, a consumer may explicitly select "favorite" classes and/or certain beverages that are grouped into a specific class. For example, a user may have a "morning" class to include beverages that include caffeine and/or a "workout" class that comprises rehydration beverages with various levels of carbohydrates that a user may select depending on the intensity of the workout.

In other embodiments, a computer-readable medium may determine one or more classes (or beverages displayed within a class) based upon the user's past purchasing or ordering decisions. Yet in other embodiments, one or more classes (or beverages) may be determined according to promotional considerations and/or upcoming events, such as holidays. In various embodiments, the display of possible beverage for selection may be adjusted based upon the levels or presence of specific ingredients detected in dispensing system 102/202. Further, actual logos and/or icons may be used in conjunction with or in lieu of any graphical configurations, including text. Those skilled in the art will also understand that non-interactive displays may also be used to display a graphical user interface, such as interface 600.

The user input received at 502 may be transmitted as a mechanical, electrical, or mechanical-electrical input. In one embodiment, a user input may be received through a local area network (LAN) and/or a wide area network (WAN), such as the Internet through a network connection, such as network connection 212 (shown in FIG. 2). Dispensing systems 102/202 (and other devices) may be connected to a communication network via twisted pair wires, coaxial cable, fiber optics or other media. Alternatively, radio waves may be used to connect one or more beverage dispenser systems to the communication network.

In one embodiment, a touch screen may be configured to allow a user to first select a specific brand of beverage, such as a particular juice from a plurality of fruit juices (e.g., from class 610). The selection of a specific brand of a beverage may follow a consumer selecting a class from a group of beverage classes. For example, the menu depicting the group of classes 602 may be replaced by another menu of different specific beverages within that class upon selection. In other embodiments, the menu depicting the group of classes 602 may remain at least partially visible. For example, a consumer may select class 604 which includes several colas. Upon selecting class 604, the user may be presented with a menu of several different "brands" of cola (see menu 612), such as "BRAND A" 614, "BRAND A Diet 616," which could represent Pepsi-Cola® and Diet Pepsi-Cola®, respectively. Other options may include "BRAND B" 618 and "BRAND B Diet" 620, which may in certain embodiments, represent Mountain Dew® and Diet Mountain Dew, respectively. Further options are provided as "BRAND C" 622 and "BRAND C Diet" 624.

In certain embodiments, a user input device, such as the touch screen may allow a user to pick a specific commercially available beverage and further refine the ingredients to be dispensed to form a similar beverage. For example, a processor in operative communication with a memory (such as computer-readable medium 204) may store a plurality of beverage formulation recipes. Thus, the first user input received at step 502 may select a one of the plurality of beverage options for further refinement before dispensing.

A second user input may be received at step 504. In certain embodiments, the second input is configured to modify a concentration of a first ingredient within the selected recipe. In one embodiment, the first ingredient may be a caloric sweetener. As discussed above, recent dietary concerns focus on reducing natural sugars, such as sucrose and/or high fructose corn syrup (HFCS). Thus, the second user input, may indicate that a consumer wishes to reduce the sugar content of the beverage formulation recipe. Yet in other embodiments, the user may wish to increase the natural sugars. For example, the consumer may have selected a diet beverage (i.e., the beverage formulation depicted by menu selection 616). Thus, the consumer may wish to adjust the flavor profile of the diet beverage to include a more natural sugar taste. In one embodiment, a display device may display an indication of the sugar level of the selected beverage formulation. For example, GUI 600 shows sugar level indicator 626 which may graphically shows the sugar level. The indication of the sugar(s) may be shown by different measurements. For example, in one embodiment, the total calories may be displayed to the user. In another embodiment, the weight of the ingredients (such as one or more sugars) may be displayed. In other embodiments, the volumetric measurement could be displayed. Still yet, the overall percentage of the ingredient could be displayed. In certain embodiments, the consumer may be able to selectively determine how the information is displayed. Furthermore, the displaying of the information may be done with objective values, such as using numerical measurements or estimates, or subjectively, such as color coding where "red" could suggest unhealthy levels, such as high sugar content, and "blue" could mean healthy levels, such as low sugar content. In certain embodiments, both objective and subjective measurements or estimates could be provided.

In certain embodiments, a consumer may adjust the sugar level indicator 626 to adjust the quantity (concentration) of sugar of the selected beverage formulation recipe. In embodiments comprising a touch screen as a user input device, a consumer may adjust the concentration by touching or sliding their finger or other device over a portion of the sugar level indicator 626. Other input devices may be used in combination with or in lieu of a touch screen. For example, a consumer may enter alphanumeric inputs and/or use arrow keys on a keypad. Other possible user input devices may allow a consumer to swipe a card having electronic information and/or provide information through use of an optical, magnetic, RFID, and/or biometric sensors. As discussed above, one or more user inputs may be received through a communication network, such as a LAN or the Internet.

At step 506, the concentration of at least one second ingredient may be automatically adjusted in response to the second user input to form a recipe of a modified beverage formulation. For example, merely adjusting one or more sugars in a cola beverage will not only reduce the flavors associated with those ingredients, but may drastically affect the impact of other ingredients which may have been masked by the sugars and/or react with the sugars (or any other ingredient). For example, reducing HFCS and/or sucrose in cola beverages may result in the consumer noticing an unpalatable taste from excessive carbonation from carbon dioxide, which provides carbonic acid. Thus, in one embodiment, the reduction of sugars at step 504 results in the automatic reduction of carbon dioxide in the recipe for the modified beverage formulation. In other embodiments, the carbon dioxide levels may be left unaltered; however, levels of other acids may be adjusted. For example, in one embodiment, citric acid levels may be adjusted based upon the consumer selecting the adjustment of the first ingredient, such as sugar. Those skilled in the art will realize that other acids, including but not limited to: lactic, malic, and other acids used in food and beverage applications may be adjusted within the scope of this disclosure. In one embodiment, one or more acids may be blended and/or stored with other ingredients, including but not limited to: caffeine, ginseng, guanine, and other acids or buffers.

Thus, certain embodiments of this disclosure permit the automatic adjustment of a non-sweetener ingredient based upon a consumer requesting the adjustment of a sweetener. In such embodiments, however, levels of a different sweetener ingredient may also be adjusted; however, it could be accompanied by an adjustment to a non-sweetener ingredient. Further embodiments, however, are directed towards automatically adjusting (increasing, decreasing, adding or removing) a concentration of an ingredient comprising a sweetener upon a consumer adjusting the concentration of another sweetener. For example, it is known that many sweeteners have various strengths of sweetness when compared to sugar. Further, as discussed above, the interaction of several different ingredients may provide a unique flavor profile that may have to be compensated for. In certain embodiments, the reduction of a sweetener may be (either partially or wholly) compensated with the addition of other sweeteners.

Exemplary sweeteners suitable for use in various embodiments of the beverages disclosed here include non-nutritive natural and artificial or synthetic sweeteners. Suitable non-nutritive sweeteners and combinations of such sweeteners may be selected for the desired nutritional characteristics, taste profile for the beverage, mouthfeel and other organoleptic factors. Non-nutritive sweeteners suitable for at least certain exemplary embodiments include, for example, peptide based sweeteners, e.g., aspartame, neotame, and alitame, and non-peptide based sweeteners, for example, sodium saccharin, calcium saccharin, acesulfame potassium, sodium cyclamate, calcium cyclamate, neohesperidin dihydrochalcone, and sucralose. Alitame may be less desirable for caramel-containing beverages where it has been known to form a precipitate. In certain exemplary embodiments the beverage product employs aspartame as the sweetener, either alone or with other sweeteners. In certain other exemplary embodiments the sweetener comprises aspartame and acesulfame potassium. Other non-nutritive sweeteners suitable for at least certain exemplary embodiments include, for example, sorbitol, mannitol, xylitol, glycyrrhizin, D-tagatose, erythritol, meso-erythritol, malitol, maltose, lactose, fructo-oligosaccharides, Lo Han Guo juice concentrate, Lo Han Guo powder of mogroside V content from 2 to 99%, rebaudioside A, stevioside, other steviol glycosides, stevia rebaudiana extracts acesulfame, aspartame, other dipeptides, cyclamate, sucralose, saccharin, xylose, arabinose, isomalt, lactitol, maltitol, trehalose, and ribose, and protein sweeteners such as monatin, thaumatin, monellin, brazzein, L-alanine and glycine, related compounds, and mixtures of any of them. Lo Han Guo, steviol glycosides, e.g. rebaudiosides, steviosides and related compounds, as discussed further below, are natural non-nutritive potent sweeteners In one embodiment, flavor oils, such as lemon, lime, lemon-lime, orange, and combinations thereof may be suspended in an emulsion may be added, increased or decreased. In yet other embodiments, extracts dissolved in alcohol may be adjusted. Those skilled in the art with the benefit of this disclosure will appreciate that any food or beverage-safe sweetener may be used without departing from the scope of this disclosure. Thus, in certain embodiments, the reduction of sugars may result in the reduction of an acid source, such as carbon dioxide and the increase in another sweetener, such as flavor oil. In certain embodiments, the automatic adjustment allows the beverage producer to maintain quality over a branded beverage while allowing the consumer to reduce some or all of the attributes that the particular consumer may deem to be negative (i.e., high sugar content).

In certain embodiments, one or more adjusted ingredients that are present within the recipe of the modified formulation may not have present in the original beverage formulation. In one embodiment, the concentration of at least one second ingredient may comprise about 0% of the recipe for the beverage formulation and about greater than 0.5% of the recipe for the modified beverage formulation. Likewise, in other embodiments, the concentration of at least one second ingredient may comprise at least about 0.5% of the recipe for the beverage formulation and about 0% of the recipe for the modified beverage formulation.

At optional step 508, an indication of the adjusted concentration of one or more of the adjusted ingredients may be displayed to the user on a display device. Using FIG. 6 as an illustrative example, the visual depiction of the reduction of sugars from level marker 628 to level marker 630 on the sugar level indicator 626 may result in the depicted level of carbon dioxide shown in CO2 level indicator 632 to move from level marker 634 to level marker 636. In other embodiments, visual depictions of other altered ingredients may be presented. In one embodiment, a user may "cycle" through different ingredients and compare the amount of one or more ingredients of the modified beverage formulation against the amount of the same ingredient within the original beverage formulation.

Other visual indicia, such as indicia 638 may be modified in accordance with one or more received user inputs. For example, indicia 638 which could resemble a beverage container may be "filled" with a liquid representing the beverage to be dispensed. For example, if a user selects a cola beverage, the depicted beverage container may be "filled" with a brown colored liquid, whereas if the consumer selects a energy drink, the beverage container depicted by indicia 638 may be "filled" with a different color. Further, the graphical representation of the beverage may be adjusted as the consumer adjusts the ingredients. For example, if a consumer reduces the carbon dioxide to be dispensed into the beverage, the graphical indicia 638 may be adjusted to make it appear that fewer bubbles in the depicted carbonated beverage.

Step 510 may be implemented to determine if further user inputs are received. If no further user inputs are received, then step 512 may be implemented to dispense a serving of the modified beverage formulation. Alternatively, step 514 may decipher further user inputs. For example, a user input may be received to confirm the dispensing of the modified beverage formulation. In other embodiments, the consumer may not want the beverage formulated created by the automatic adjustment. Thus, in one embodiment, a user input may be received that requests the dispensing of a beverage according to a recipe of a beverage modified according to the consumer's requested alteration, however, without the automatic adjustment of the at least one second ingredient.

In yet other embodiments, the user may desire to review and/or revise the recommended concentrations that were automatically adjusted. For example, if an initial concentration of carbonation was at 100% and was reduced to about 60% during the automatic adjustment of step 506, the user may increase the carbonation (for example, to about 70%) or alternatively in the lower direction to further reduce the carbonation.

Figure 7:
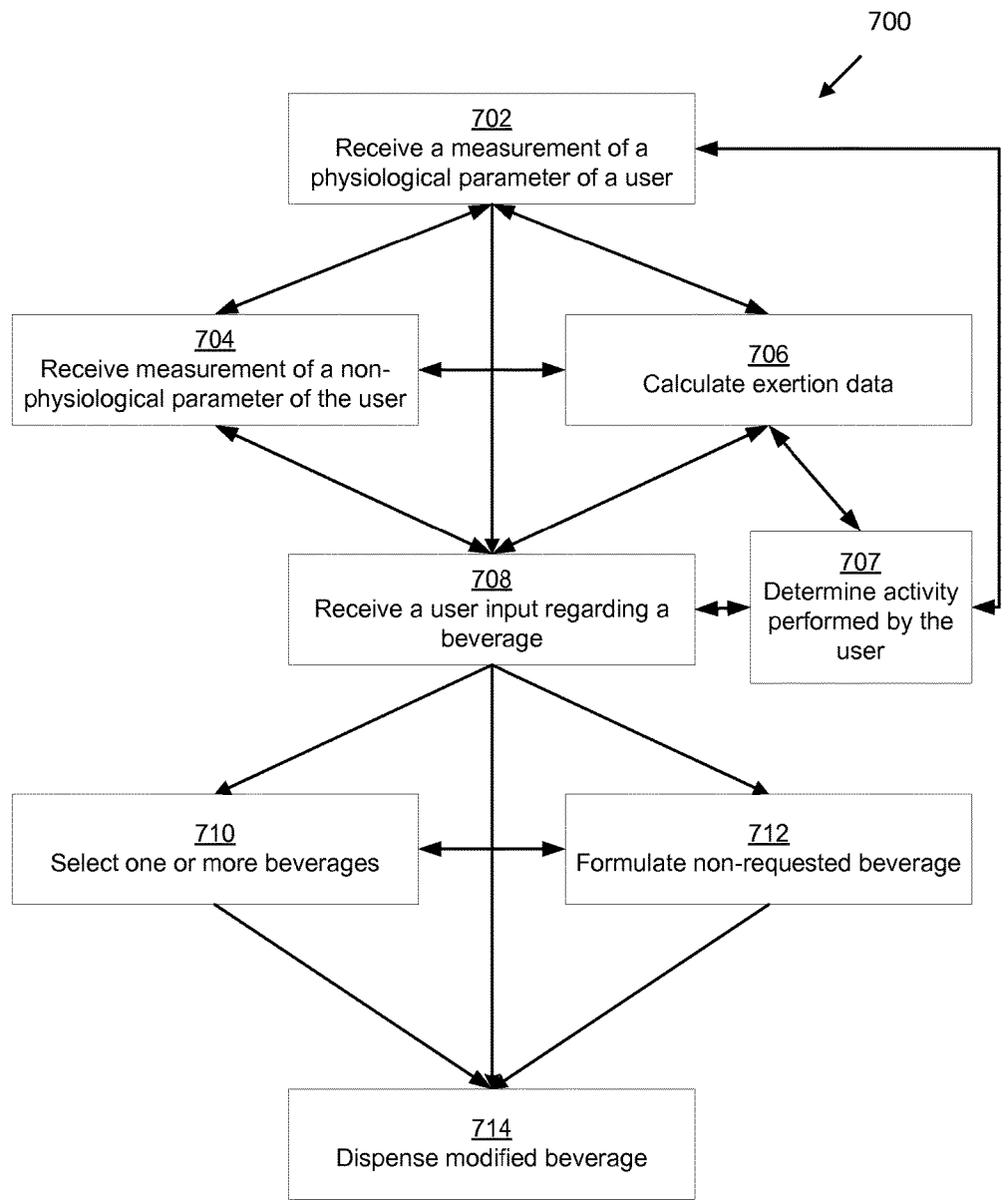
FIG. 7 is a flowchart of an exemplary method in accordance with one embodiment of the invention.

Further aspects of the invention are directed towards the formulation of beverages, or other foodstuffs, based upon the physiological parameters of a user. FIG. 7 is a flowchart showing one exemplary process 700 for dispensing a beverage in accordance with one embodiment of the invention. Process 700 is shown for illustrative purposes only and those skilled in the art with the benefit of this disclosure will readily appreciate that process 700 may include additional or fewer sub-processes. Moreover, the order of process 700 is also for illustrative purpose and may be conducted in almost any order.

In one embodiment, block 702 may be initiated to measure of a physiological parameter of a user. The physiological parameter may be measured automatically, such that the user is not required to determine or manually enter the parameter. Thus, unlike certain prior art systems, the collection of one or more physiological parameters is not subject to guessing or entry error. In this regard, users often engage in physical activity to lose weight, thus reliance on the user to accurately enter the data may be influenced by their desire to lose the weight and/or peer pressure from other individuals. Therefore, automated collection of physiological data is preferred in several instances.

In one embodiment, the measurement of one or more physiological parameters may be transmitted directly to a beverage dispenser. For example, the measurements may be electronically transmitted to dispensers 102 and/or 202, shown in FIGS. 1 and 2, respectively. In one embodiment, one or more measurements may be wirelessly transmitted to dispenser 202 through network connection 212. As seen in FIG. 2, beverage dispenser 202 comprises computer-readable medium 204 which may be utilized to store measurement data. In one embodiment, the data may be collected and stored in real-time. In another embodiment, the data may be stored at beverage dispenser 202 a later time, such as when the user requests a beverage (discussed in more detail below). In one embodiment, a wireless device measures the physiological parameter, which is directly transmitted to the beverage dispenser 202. In another embodiment, the wireless transmission may travel through one or more devices, such as a router, before arriving at the beverage dispenser 202. The beverage dispenser 202 further comprises processor 206, which may be used to perform analysis of the data.

The device measuring the physiological parameters may also be associated with the beverage dispenser 202. For example, in one embodiment, the dispenser may dispense one or more devices 155a that the user may utilize before and/or while obtaining a beverage. In one embodiment, a user may select (including providing payment for) a beverage, however, the beverage is not immediately dispensed. Rather, the device 155a configured to measure one or more parameters may be provided to a user. The device 155a may communicate with the dispenser during physical exertion, such as an exercise routine, and a beverage may be later dispensed. Other measuring devices, such as devices 155b that measure non-physiological parameters, may also be dispensed from the beverage dispenser 202. Exemplary devices 155a, 155b are discussed in more detail below in regards to block 704.

In certain embodiments, a biosensor 151 (FIG. 1) may be wearable by the user. The biosensor 151 may be configured to be worn during rigorous physical exertion, such as running, swimming or biking. In one embodiment, the biosensor 151 is part of a wristband. The biosensor 151, however, may be any wearable device, such as forming part of a headband, anklet, necklace, armband, or combinations thereof. In another embodiment, the physiological measuring device (an/or other measuring devices) may be associated with a beverage (or food) receptacle. In one embodiment, a beverage receptacle 203 may be reusable, such that it may receive multiple servings of beverages from the beverage dispenser 202. A device 205 may be attachable to a portion of a beverage receptacle 203 that is usable with beverage dispenser 202. In certain embodiments, the device 205 may be removably attached to the beverage receptacle 203. The device 205 may be attachable or form part of a lid, cap, neck, and/or body of the beverage receptacle 203. The parameter(s) that the device 205 may measure may be dependent on the beverage(s) obtained and/or the quantity of beverage(s) obtained.

The physiological parameter may be noninvasively measured from one or more bodily fluids, including but not limited to: sweat, saliva (including breath analysis), tears, urine and combinations thereof. Any physiological parameter obtained from a bodily fluid is within the scope of the invention, including but not limited to: pH, electrolyte levels, temperature, fluid loss, rate or amount of electrolyte loss, fluid electrolyte concentration, fluid osmolality, and/or changes to any parameters over time, such as an increase or a threshold rate of an increase in any parameter. As one embodiment, the value of an electrolyte level may not only be measured, but also the rate at which the electrolyte is are being depleted. Other parameters may be based upon non-fluid mediums, including but not limited to: pulse, blood pressure, skin tone, temperature, Body mass index (BMI), respiration rate, weight, changes to any parameters such as an increase or a threshold rate of increase for any parameter. As one example, the blood pressure may be one parameter, however, the duration of blood pressure over a predefined threshold may also be another parameter being measured.

In certain embodiments, other non-physiological data may be collected (see, e.g. block 704). Exemplary non-physiological data may include, for example, environmental and/or biographical data. Exemplary environmental data may include, but is not limited to temperature, humidity, altitude, and combinations thereof. Biographical data may be any data relating to the user that is not automatically collected by a device. Exemplary biographical data may include, but is not limited to: sex, age, race, height, behavioral data, diet, fitness level, physical appearance, cognitive capability, previously-recorded recorded patient biometric data and/or trends in historical patient biometric data may also be used.

Further embodiments may include the calculation of exertion data (see, e.g., block 706). The calculation of exertion data may include one or more inputs from physiological and/or non-physiological parameters (such as from blocks 702 and/or 704, among others). In one embodiment, the calculation of exertion data may receive inputs regarding at least one physiological parameter (but may also include inputs from one ore more non-physiological parameters) to derive a second physiological parameter not being measured. Such calculation may be beneficial to reduce costs associated with multiple sensors, reduce frustration of wearing or locating multiple physiological measuring devices, and/or allow more accurate assessment of the user's exertion level.

In one embodiment, a device may measure electrolytic levels in sweat. Used alone, the device may only indicate that a user lost little quantities of electrolytes during physical activity. This, however, may not provide the most accurate analysis of the user. Calculating the exertion data, whether from the physiological measurements, alone or with other data, may be used to estimate a muscle usage and/or determine what activity the user was performing (block 707), such as lifting weights. For example, by measuring the motion of a user and/or the time a user undertakes a specific activity, the calculation may determine the user was lifting weights, performing yoga, running on a treadmill, or other activities. In one embodiment, stress of certain muscles or other organs of the body may be estimated without receiving data regarding that organ or system from a physiological measuring device. This may be useful, for example, to prevent the invasive collection (such as collecting blood through needles) to measure blood factors indicative of such activity. As discussed below, such information may be useful in determining to formulate one or more recipes.

Block 708 may be implemented in certain embodiments to receive a user input. The user input may be received as a mechanical, electrical, or mechanical-electrical input. In one embodiment, a user input may be received through a local area network (LAN) and/or a wide area network (WAN), such as the Internet through a network connection, such as network connection 212 (shown in FIG. 2). In one embodiment, a touch screen may be configured to allow the reception of a user input.

The type of user input may vary depending on the embodiment being implemented. In one embodiment, the user input of block 708 may select a class of beverages, such as exemplary classes: juices, energy drinks, and hydration beverages. For example, in one embodiment, the user input received at block 708 may select hydration beverages, and based upon that selection, block 710 may be implemented to select one or more beverage formulations within that class. In one embodiment, the selected beverage formulation is a branded-beverage. For example, during an exercise routine, physiological data may indicate that a user has lost a modest level of electrolytes and has also been lifting weights. Thus, when a user input is received at block 708 that selects hydration beverages, a specific formulation for both endurance and restoring electrolytes may be selected. In another embodiment, the user may be given an option of two or more beverages, such as having different flavors. In one embodiment, block 712 may be implemented, independently of or in conjunction with block 710 to modify the branded beverage. For example, it may be determined that the branded beverage may provide too much of at least one electrolyte, therefore, block 712 may be implemented to reduce the level of that at least one electrolyte in the recipe. Thus, in accordance with certain embodiments, beverage dispensers 202 may maintain the quality associated with a branded beverage while permitting consumers to enjoy the personalized beverages.

In another embodiment, block 712 is initiated without block 710. For example, the user selection at block 708 may select a specific beverage, for example, the user may select a specific hydration beverage, such as G2®. Step 712 may then formulate a non-requested formula. As used herein, a non-requested formula is any recipe that differs from the requested formula, such as for example, by having different ingredients and/or levels of the same ingredients. For example, the G2® may be modified to include more natural sugars and/or one or more electrolytes. In one embodiment, sodium chloride, sodium citrate, mono-potassium phosphate, quercetin, and combinations thereof, may be separate ingredients that may be individually adjusted.

In one embodiment, upon the user selecting a class of beverages or a specific beverage at block 708, a menu may be provided to suggest alternative formulas to the user, such as a modified G2® recipe, a branded or novel Gatorade® recipe, a branded or novel Propel® recipe, or combinations thereof. In one embodiment, user input device (such as input device 208) may comprise a touch screen that is in operative communication with electronic circuitry 129 to display the menu and/or other options to the user. In this regard, electronic circuitry 129 may include computer-readable medium 204 which may store one or more recipes for beverage formulations. In accordance with further embodiments, a user input (such as received at block 708) may allow a user to adjust one or more ingredients of the formulation. For example, after a workout, users often desire less carbonation in their cola beverages, or more electrolytes in their hydration beverages. As discussed above, for example, in relation to FIGS. 5 and 6, the adjustment of one ingredient may cause the adjustment of at least one other ingredient. The adjustment of an ingredient may be part of the user input of block 708 and/or after either block 710 and/or block 712 have commenced. In one embodiment, at least one ingredient that is added or adjusted in a micro ingredient.

Block 714 may be implemented to dispense the recipe formulated at blocks 710 and/or 712. The dispensing of the beverage may be performed in accordance with any embodiment disclosed herein. In one embodiment, the beverage is dispensed from beverage dispenser 102/202. Beverage dispenser 102/202 may be configured to adjust the dispensing of one ingredient based upon one or more properties of another ingredient. Examples of this are described in relation to FIGS. 1-4. Further, certain embodiments allow the accurate measuring and dispensing of non-Newtonian fluids. In one embodiment, beverage dispenser 202 is a unitary dispensing apparatus that is configured to micro dose one or more ingredients. In one embodiment, sodium chloride, sodium citrate, mono-potassium phosphate, quercetin, and combinations thereof, may each be dispensed individually as micro ingredients. In one embodiment, beverage dispenser 202 may comprising an individual micro dosing module 157 with variable viscosity capabilities to accurately micro dose a plurality of different micro ingredients 159, 161. In one embodiment, the module 157 may be about 0.5 inches thick, 1.5 inches deep, and about 2 inches high. In other embodiments, two or more micro dosing modules may be used. In one embodiment, the modules are about 1.5 inches deep and about 2 inches high, where the thickness is 0.5 inches for each individual module. Those skilled in the art will readily appreciate that the dimensions provides for thickness, depth, and height are for illustrative purposes, and the dimensions are interchangeable. In certain embodiments, static mixing of multiple ingredients (one or more micro ingredients 159, 161, flavor syrups, water, etc.) may be performed near the nozzle 122 (shown in FIGS. 1 and 2). This may allow more optimal operation and/or sanitary characteristics.

One or more of the beverage formulation recipes may be stored on a computer-readable medium, either locally or remotely. For example, in one embodiment, the recipe of the modified beverage formulation may be stored. In another embodiment, the recipe of the beverage that was ultimately dispensed may be stored. One or more dispensing systems 202 may be in communication with each other and readily transmit and receive information regarding other dispenser systems, including a unique formula dispensed to a particular user. In one embodiment, a plurality of dispensing systems may each be coupled to each other through a central server. Yet in another embodiment, the dispensing systems may communication directly with each other. Thus, in one or more embodiments, electronic circuitry 129 may include computer-executable instructions for transmitting information to other dispensers and/or a server.

What is claimed is:

1. A method of displaying a beverage selection at a beverage dispensing device comprising:
   receiving, at a beverage dispensing device, a first user input corresponding to a selection of a beverage having a first ingredient and a second ingredient;
   displaying, at a display device of the beverage dispensing device, a graphical representation of the beverage including a first concentration of the first ingredient and an amount of the second ingredient;
   receiving, at the beverage dispensing device, a second user input corresponding to an adjustment of the first concentration of the first ingredient of the beverage;
   modifying the graphical representation of the beverage based on the second user input to provide an indication of the adjusted first ingredient;
   comparing the received modification to a taste profile of the selected beverage and determining, based on the taste profile, the amount of the second ingredient needed to ensure that the beverage conforms to the taste profile;
   updating automatically the amount of the second ingredient of the beverage based on the adjustment of the first concentration of the first ingredient and the amount of the second ingredient needed to ensure that the beverage conforms to the taste profile;
   updating the graphical representation of the beverage based on the update to the amount of the second ingredient;
   receiving, at the beverage dispensing device, a dispense user input to dispense the beverage including the adjusted first concentration of the first ingredient and the automatically adjusted amount of the second ingredient; and
   dispensing the beverage including the adjusted first concentration of the first ingredient and the automatically adjusted amount of the second ingredient.

2. The method of claim 1 wherein:
the graphical representation of the beverage comprises i) a first graphic depicting a beverage container, ii) a second graphic depicting a volume of liquid within the beverage container, and iii) a third graphic depicting the first ingredient.

3. The method of claim 2 wherein:
the third graphic depicting the first ingredient comprises an indication of at least one measurement associated with the first ingredient; and
the at least one measurement comprises at least one of an amount of calories of the first ingredient,
a weight of the first ingredient,
a volume of the first ingredient, and a
percentage of the first ingredient.

4. The method of claim 3 further comprising:
receiving, at the beverage dispensing device, a third user input corresponding to a selection of a measurement associated with the first ingredient; and
updating the graphical representation of the beverage based on the third user input such that the third graphic depicting the first ingredient comprises an indication of the measurement selected.

5. The method of claim 2 wherein:
the first ingredient is sugar.

6. The method of claim 1 further comprising:
displaying, at the display device, one or more selectable beverage class indicators;
receiving, at the beverage dispensing device, a third user input corresponding to a selection of one of the selectable beverage class indicators; and
displaying, at the display device, one or more selectable beverage indicators based on the selection of one of the selectable beverage class indicators.

7. The method of claim 6 wherein:
the one or more selectable beverage class indicators include at least one of
i) a first beverage class indicator identifying a beverage brand,
ii) a second beverage class indicator identifying a beverage type,
iii) a third beverage class indicator identifying a beverage ingredient, and iv) a fourth beverage class indicator identifying a promotional event.

8. The method of claim 7 wherein:
the one or more selectable beverage class indicators further include at least one of
v) a fifth beverage class indicator that, when selected, causes the one or more selectable beverage indicators to include a selectable beverage indicator associated with a favorite beverage of a user, and
vi) a sixth beverage class indicator that, when selected, causes the one or more selectable beverage indicators to include a selectable beverage indicator associated with a beverage previously purchased by the user.

9. A beverage dispensing device comprising:
an input device configured to receive a first user input corresponding to a selection of a beverage and second user input corresponding to an adjustment of a first concentration of a first ingredient of the beverage;
a display device configured to display a graphical representation of the beverage including the first concentration of the first ingredient;
memory storing computer-readable instructions that, when executed, cause the display device to:
modify the graphical representation of the beverage based on the second user input to provide an indication of the adjusted first ingredient;
compare the received modification to a taste profile of the selected beverage;
determine, based on the taste profile, an amount of a second ingredient to conform the beverage to the taste profile;
update automatically the amount of the second ingredient of the beverage based on the adjustment of the first concentration of the first ingredient and the amount of the second ingredient needed to ensure that the beverage conforms to the taste profile;
update the graphical representation of the beverage based on the update to the amount of the second ingredient;
provide a color-coded assessment of the nutritional values of the resulting beverage based on a comparison of the nutritional values of the resulting beverage and subjective measurements stored in the memory; and
a dispensing head to dispense the beverage including the adjusted first concentration of the first ingredient and the automatically adjusted amount of the second ingredient.

10. The beverage dispensing device of claim 9 wherein:
the graphical representation of the beverage comprises i) a first graphic depicting a beverage container, ii) a second graphic depicting a volume of liquid within the beverage container, iii) a third graphic depicting the first ingredient, and iv) a fourth graphic depicting the second ingredient.

11. The beverage dispensing device of claim 10 wherein:
the third graphic depicting the first ingredient comprises an indication of at least one measurement associated with the ingredient; and
the at least one measurement comprises at least one of:
an amount of calories of the first ingredient,
a weight of the first ingredient,
a volume of the first ingredient, and
a percentage of the first ingredient.

12. The beverage dispensing device of claim 11 wherein:
the input device is further configured to receive a third input corresponding to a selection of a measurement associated with the first ingredient; and
the instructions, when executed, further cause the display device to update the graphical representation of the beverage based on the third user input such that the third graphic depicting the first ingredient comprises an indication of the measurement selected.

13. The beverage dispensing device of claim 10, wherein the ingredient is sugar.

14. The beverage dispensing device of claim 9 wherein:
the instructions, when executed, further cause the display device to:
display one or more selectable beverage class indicators, and
display one or more selectable beverage indicators based on a third user input received at the input device that corresponds to a selection of one of the selectable beverage indicators.

15. The beverage dispensing device of claim 14 wherein:
the one or more selectable beverage class indicators include at least one of
i) a first beverage class indicator identifying a beverage brand,
ii) a second beverage class indicator identifying a beverage type, iii) a third beverage class indicator identifying a beverage ingredient, and iv) a fourth beverage class indicator identifying a promotional event.

16. The beverage dispensing device of claim 15 wherein:
the one or more selectable beverage class indicators further include at least one of v) a fifth beverage class indicator that, when selected, causes the one or more selectable beverage indicators to include a selectable beverage indicator associated with a favorite beverage of a user, and vi) a sixth beverage class indicator that, when selected, causes the one or more selectable beverage indicator to include a selectable beverage indicator associated with a beverage previously purchased by the user.

17. The beverage dispensing device of claim 9 further comprising:
a touch screen device that comprises the input device and the display device.

18. Non-transitory computer-readable media having instructions that, when executed by a processor of a beverage dispensing device, cause the beverage dispensing device to:

receive, at an input device of the beverage dispensing device, a first user input corresponding to a selection of a beverage having a first ingredient and a second ingredient;

display, at a display device of the beverage dispensing device, a graphical representation of the beverage wherein the graphical representation comprises i) a first graphic depicting a beverage container, ii) a second graphic depicting a volume of liquid within the beverage container, and iii) a third graphic depicting the first ingredient of the beverage comprising an indication of a first concentration of the first ingredient;

receive, at the input device, a second user input corresponding to an adjustment of the first concentration of the first ingredient of the beverage;

modify the graphical representation of the beverage based on the second user input to provide an indication of the adjusted first ingredient;

compare the received modification to a taste profile of the selected beverage;

determine, based on the taste profile, an amount of a second ingredient to conform the beverage to the taste profile;

update automatically the amount of the second ingredient of the beverage based on the adjustment of the first concentration of the first ingredient and the amount of the second ingredient needed to ensure that the beverage conforms to the taste profile;

update the graphical representation of the beverage based on the update to the amount of the second ingredient;

receive, at the input device, a third user input corresponding to an adjustment of the automatically adjusted second ingredient;

modify the graphical representation of the beverage based on the third user input to provide an indication of the adjusted second ingredient;

receive, at the input device, a dispense user input to dispense the beverage including the adjusted first concentration of the first ingredient and the user adjusted amount of the second ingredient; and dispense the beverage including the adjusted first concentration of the first ingredient and the user adjusted amount of the second ingredient.

19. The non-transitory computer-readable media of claim 18 wherein the instructions, when executed, further cause the beverage dispensing device to:

cycle through a plurality of ingredients of the beverage at the display device in response to additional user input received at the input device.

* * * * *